(12) United States Patent
Fuchs et al.

(10) Patent No.: US 7,084,107 B1
(45) Date of Patent: Aug. 1, 2006

(54) METHODS FOR STABILIZING LIQUID NUTRITIONAL PRODUCTS AND PRODUCTS SO STABILIZED

(75) Inventors: Eileen C. Fuchs, Monroe, CT (US); Chandrasekhara Reddy Mallangi, New Milford, CT (US); Kjerstin Carlsson, Bern (CH); Axel Syrbe, Clarens (CH); Reinhard Behringer, Oberdiessbach (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 09/959,131

(22) PCT Filed: Apr. 13, 2000

(86) PCT No.: PCT/EP00/03504

§ 371 (c)(1),
(2), (4) Date: Mar. 20, 2002

(87) PCT Pub. No.: WO00/60953

PCT Pub. Date: Oct. 19, 2000

(51) Int. Cl.
*A23C 21/00* (2006.01)
*A61K 31/736* (2006.01)

(52) U.S. Cl. .............. 514/2; 514/54; 514/60; 530/350; 426/41; 536/45; 536/52

(58) Field of Classification Search .......... 514/2, 514/54, 60; 530/350; 536/45, 52
See application file for complete search history.

(56) References Cited

U.S. PATENT DOCUMENTS

| | | | | |
|---|---|---|---|---|
| 5,215,777 A | * | 6/1993 | Asher et al. | 426/565 |
| 5,470,839 A | * | 11/1995 | Laughlin et al. | 514/53 |
| 5,486,375 A | | 1/1996 | Yoder et al. | |
| 5,549,905 A | * | 8/1996 | Mark et al. | 424/439 |
| 5,776,887 A | * | 7/1998 | Wibert et al. | 514/2 |
| 5,968,586 A | * | 10/1999 | Etzel | 426/657 |
| 6,355,609 B1 | * | 3/2002 | Mallangi et al. | 514/2 |

FOREIGN PATENT DOCUMENTS

EP  0 462 012 A2  12/1991
IT  2 518 372  12/1981

* cited by examiner

*Primary Examiner*—Bruce R. Campbell
*Assistant Examiner*—Anish Gupta
(74) *Attorney, Agent, or Firm*—Bell, Boyd & Lloyd LLC

(57) ABSTRACT

Nutritional solutions and methods of making same are disclosed. The solutions include protein, lipid, and a carbohydrate source including high amylose starch and guar gum.

26 Claims, 1 Drawing Sheet

METHODS FOR STABILIZING LIQUID NUTRITIONAL PRODUCTS AND PRODUCTS SO STABILIZED

BACKGROUND OF THE INVENTION

The present invention relates generally to the treatment of patients and products for treating patients. More specifically, the present invention relates to enteral solutions for providing nutritional support to patients.

It is of course known to feed patients, requiring nutrition in a hospital or other health care setting (including a home), with enteral or parenteral nutrition solutions. Parenteral nutrition solutions include solutions that are infused intravenously into the patient through an IV system. Enteral products include products that are fed into a patient's gastrointestinal system typically through a nasogastric feeding tube.

There are a variety of different products that have been designed to provide enteral nutritional support to a patient. Some of these products are designed to provide all necessary nutrients. On the other hand, a number of the enteral products can also be used as supplements to a normal diet. Some of these products are directed to specific disease states while other products are more generic and broad based for providing nutritional support to patients who cannot obtain necessary nutrients through traditional means of eating food.

Depending on the indication of the enteral solution, the formulation may change. For example, certain patient populations may require increased protein levels. Likewise, certain patient populations may require hydrolyzed or non intact protein.

Nutritional enteral products include: Glytrol®; Nutri-Hep®; NutriVent®; Probalance®; RenalCal®; Crucial®; Peptamen®; Peptamen VHP®; NuBasics®; NuBasics VHP®; Entrition®; Nutren®; Reablian®; Reablian HN®; Replete®; Travasorb®; Peptamen Jr.®; and Elementra®, all available from Nestlé Clinical Nutrition, Deerfield, Ill. A number of other manufacturers sell enteral nutrition products including Ross Laboratories a division of Abbott Laboratories, Mead Johnson, and Novartis.

In certain enteral products serum separation has been observed. This physical instability reduces the product's elegance. Further, it may create an adverse impression in the minds of some consumers regarding the product's quality and acceptability, even though such serum separation does not adversely affect the quality or efficacy of the product.

There is therefore a need for improving the stability of at least certain enteral solutions.

SUMMARY OF THE INVENTION

The present invention provides methods for stabilizing nutritional products including enteral solutions. Additionally, the present invention provides solutions so stabilized.

To this end, the present invention provides an enteral formula comprising a protein source, a lipid source, and carbohydrates including high amylose starch and guar gum.

In an embodiment, the protein source comprises approximately 10% to about 25% of the total calories.

In an embodiment, the lipid source comprises approximately 25% to about 50% of the total calories.

In an embodiment, carbohydrates comprise approximately 40% to about 60% of the total calories.

Preferably, the high amylose starch comprises at least approximately 50% amylose.

In an embodiment, high amylose starch and guar gum as a total comprise approximately 2.25% to about 7.5% of the total caloric content.

In an embodiment, high amylose starch comprises approximately 2% to about 6.5% of the total caloric content.

In an embodiment, the product includes xanthan.

In an embodiment, guar gum comprises 0.25% to about 1:0% of the total caloric content.

In an embodiment, the weight ratio of high amylose starch to guar gum is approximately 2.5:1 to 16:1.

In an embodiment, the product includes carrageenan.

In another embodiment the present invention provides an enteral product comprising a hydrolyzed whey protein source, a source of lipids, and a sufficient amount of a stabilizer to prevent serum separation, the stabilizer including high amylose starch and guar gum.

In an embodiment, the protein source comprises approximately 10% to about 25% of the total calories.

In an embodiment, the lipid source comprises approximately 25% to about 50% of the total calories.

In an embodiment, high amylose starch and guar gum as a total comprise approximately 2.25% to about 7.50% of the total caloric content.

In an embodiment, high amylose starch comprises approximately 2.0% to about 6.5% of the total caloric content.

In an embodiment, guar gum comprises 0.25% to about 1.0% of the total caloric content.

In an embodiment, the weight ratio of high amylose starch to guar gum is approximately 2.5:1 to 16:1.

In an embodiment, the source of lipids includes medium and long chain triglycerides.

In an embodiment, the product at 1500 Kcal provides at least 100% of the U.S. RDA of vitamin and minerals.

In an embodiment, the product has a caloric content of approximately 1.0 Kcal/ml.

In yet a further embodiment of the present invention, a method of stabilizing an enteral solution is provided. The method comprises the step of adding to an enteral solution a stabilizing amount of high amylose starch and guar gum.

Accordingly, an advantage of the present intention is to provide nutritional products including enteral solutions having greater stability.

A further advantage of the present invention is to provide a stabilizer system for nutritional products.

Still further, an advantage of the present invention is to provide nutritional products that have improved compatibility of ingredients, especially starches and gums.

Further, an advantage of the present invention is to provide an enteral solution including hydrolyzed whey protein having a stabilizing combination of starch and gum.

Moreover, an advantage of the present invention is to provide methods of stabilizing enteral solutions.

Additionally, an advantage of the present invention is to provide improved enteral solutions.

Furthermore, an advantage of the present invention is to substantially reduce if not eliminate serum separation in enteral products.

Another advantage of the present invention is to provide a method for stabilizing starch and gum combinations.

Additional features and advantages of the present invention are described in, and will be apparent from, the detailed description of the presently preferred embodiments and the figures.

DETAILED DESCRIPTION OF THE PRESENTLY PREFERRED EMBODIMENTS

Figure 1:
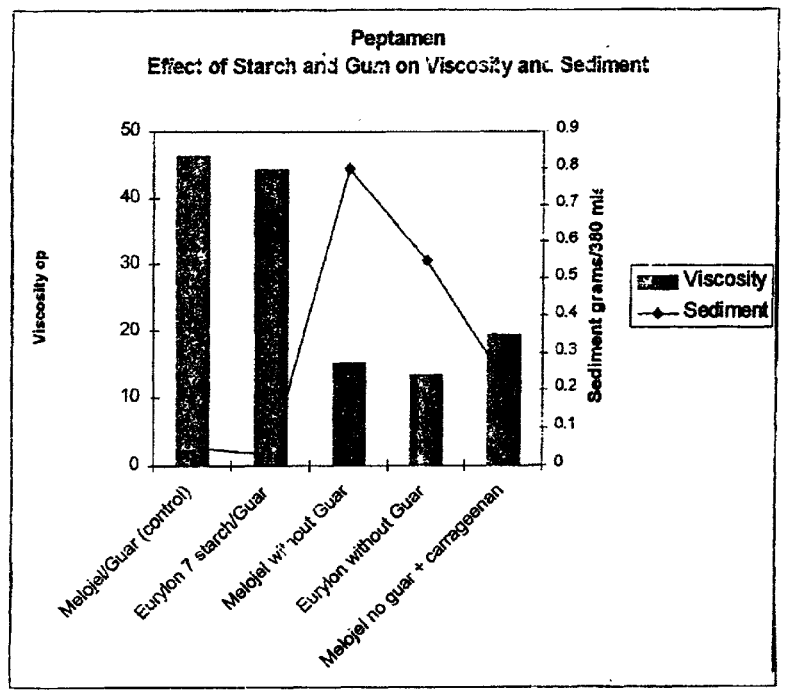
FIG. 1 illustrates graphically the effect of starch and gum on viscosity and sediment pursuant to Example No. 1.

The present invention provides methods for stabilizing nutritional products including enteral solutions. Additionally, the present invention provides nutritional products including enteral solutions so stabilized.

There has been observed, in certain enteral solutions, serum separation. It has been found, during stability studies, that serum separation in many enteral products containing hydrolyzed protein is due to the starch and gum formulation. For example, in the Nestlé product Peptamen®, polysaccharides and guar gum are used in the formula. Specifically, the polysaccharide is Melojel starch. Peptamen® has been observed in certain circumstances to suffer from serum separation. It was surprisingly discovered that the separation can be eliminated by providing a different starch and gum combination.

In this regard, it was surprisingly found that the stability of at least certain enteral products can be improved by providing a stabilizing combination of starch and gum. This starch and gum combination can be added to the product without requiring any additional label changes while at the same time eliminating any possible serum separation.

Specifically, it was discovered that the use of high amylose starch and guar gum stabilizes enteral products, especially those containing hydrolyzed protein. Preferably, the high amylose starch comprises at least approximately 50% amylose, and most preferably approximately 70% amylose. Preferably, the high amylose starch and guar gum as a combination comprises approximately 2.25% to about 7.5% of the caloric content of the product. Preferably the weight ratio of high amylose starch to guar gum is approximately 2.5:1 to 16:1; and more preferably approximately 8:1 to about 12:1. Preferably high amylose starch comprises approximately 2.0% to 6.5% of the caloric content of the product. Preferably guar gum comprises approximately 0.25% to about 1.0% of the caloric content of the product.

The product will include in addition to the stabilizing system of high amylose starch and guar gum a protein source, a lipid source, vitamins and minerals. Preferably the protein source will comprise approximately 10% to about 25%, and more preferably approximately 12% to about 20%, of the caloric content of the product. Preferably, the protein is hydrolyzed protein such as hydrolyzed whey or hydrolyzed casein. Preferably, the lipid source wilt comprise approximately 25% to about 50%, and more preferably approximately 30% to about 40%, of the caloric content of the product. Preferably, the lipids are a mixture of long chain triglycerides (LCTS) and medium chain triglycerides (MCTS). Preferably the carbohydrate source will comprise approximately 40% to about 60%, and more preferably approximately 45% to 55%, of the caloric content of the product. In a preferred embodiment, the product will provide at least 100% of the U.S. RDA of vitamins and minerals in 1500 Kcal of product (1500 mls).

By way of example, and not limitation, an example of the present invention is as follows:

| Nutrient Composition | Amount | % U.S. RDA* |
|---|---|---|
| Protein | 10 g | ** |
| Carbohydrate*** | 31.8 g | 22 |
| Fat**** | 9.8 g | ** |
| Water | 220 ml | ** |
| Vitamin A | 1000 I.U. | 20 |
| Vitamin D | 70 I.U. | 18 |
| Vitamin E | 7 I.U. | 23 |
| Vitamin K | 20 mcg | ** |
| Vitamin C | 35 mg | 58 |
| Thiamine ($B_1$) | .5 mg | 33 |
| Riboflavin ($B_2$) | .6 mg | 35 |
| Niacin | 7 mg | 35 |
| Vitamin $B_6$ | 1 mg | 50 |
| Folic Acid | 135 mcg | 34 |
| Pantoth Acid | 3.5 mg | 35 |
| Vitamin $B_{12}$ | 2 mcg | 33 |
| Biotin | 100 mcg | 33 |
| Choline | 112 mg | ** |
| Taurine | 20 mg | ** |
| L-Carnitine | 20 mg | ** |
| Calcium | 200 mg | 20 |
| Phosphorus | 175 mg | 18 |
| Magnesium | 100 mg | 25 |
| Zinc | 3.5 mg | 23 |
| Iron | 3 mg | 17 |
| Copper | .35 mg | 18 |
| Manganese | .68 mg | ** |
| Iodine | 25 mcg | 17 |
| Sodium | 125 mg | |
| **Potassium | 313 mg | ** |
| Chloride | 250 mg | ** |
| Chromium | 10 mcg | ** |
| Molybdenum | 30 mcg | ** |
| Selenium | 10 mcg | ** |

*% U.S. RDA Recommended daily allowance for adults and children 4 or more years of age
**U.S. RDA not established
***Includes high amylose corn starch—70% amylose (4% of the caloric content of the product) and guar gum (0.4% of the caloric content of the product).
****MCT provides 6.75 grams/250 ml By way of example, and not limitation, experiments relating to the present invention are as follows:

EXPERIMENT NO. 1

Peptamen® is a hydrolyzed whey protein based enteral solution which is manufactured by a UHT process and aseptically filled into cans and aseptic pouches. Serum separation has been observed in some Peptamen® products. The serum usually develops within 2 weeks and develops more rapidly at cooler temperatures (40° F. and 72° F.) than at elevated temperatures (86° F. and 100° F.).

It has been surprisingly determined that the serum separation in Peptamen® is due to thermodynamic incompatibility between the starch and the guar gum. The purpose of this study is to demonstrate the compatibility of the starches and gums and to determine the optimum polysaccharide combinations for a Peptamen® type system.

Methodology

A Peptamen® formula, based on hydrolyzed whey (see Table 1), was used as the base for evaluation of the compatibility of the starches and gums. The starches included Melojel (low amylose starch) (25% amylose from National Starch) and Eurylon 7 (high amylose starch) (70% amylose from Roquette). The gums evaluated included guar gum as well as xanthan gum (eltrol SF). A 50:50 blend of Xanthan gum and guar gum was also evaluated. In addition a blend of iota and kappa carrageenans was also evaluated to determine its effect on serum separation.

The variables were put into storage at 40° F., 72° F., 86° F. and 100° F. conditions and were evaluated on 2 week intervals for serum separation and viscosity change. In addition fresh samples were transferred from the cans into sterile jars and stored at ambient temperature for visual inspection of the samples.

that the serum separation is not related to the product viscosity in the Peptamen® regular formula (see Table 2 below). The viscosity however does appear to correlate with sedimentation (see FIG. 1).

Formulas without guar gum added had lower viscosity and greater salt sediment compared to formulas containing gum which had higher viscosity. The variable with Eurylon 7 starch alone had slightly smaller amount of sediment than Melojel (low amylose) starch alone. Carrageenan added to the Melojel starch formula increased the viscosity slightly and reduced the sediment slightly. However, the sediment TABLE No. 1

| INGREDIENT | MELOJEL LOW AMYLOSE STARCH GUAR GUM % | EURYLON 7 HIGH AMYLOSE STARCH GUAR GUM % | MELOJEL LOW AMYLOSE STARCH GUAR GUM/ CARRAGEENAN % |
|---|---|---|---|
| LIQUID HYDROLYZED WHEY | 38.593 | 38.593 | 38.593 |
| MCT OIL | 2.630 | 2.630 | 2.630 |
| SOYBEAN OIL | 0.624 | 0.624 | 0.624 |
| LECITHIN | 0.200 | 0.200 | 0.200 |
| MALTODEXTRIN 10 DE | 10.4000 | 10.9000 | 10.4000 |
| CORN STARCH-MELOJEL | 1.6100 | — | 1.6100 |
| CORN STARCH-EURYLON 7 | — | 1.1000 | — |
| GUAR GUM | 0.1177 | 0.1177 | 0.1177 |
| CARRAGEENAN VISCARIN | — | — | 0.005 |
| CARRAGEENAN SEAKEM | — | — | 0.025 |
| POTASSIUM CITRATE TRIBASIC | 0.0897 | 0.0897 | 0.0897 |
| SODIUM CITRATE* 2H2O | 0.0250 | 0.0250 | 0.0250 |
| POTASSIUM CHLORIDE | 0.0557 | 0.0557 | 0.0557 |
| SODIUM PHOSPHATE DIBASIC anhydrous | 0.0830 | 0.0830 | 0.0830 |
| CALCIUM CITRATE *4 H2O | 0.0603 | 0.0603 | 0.0603 |
| TRICALCIUM PHOSPHATE | 0.1193 | 0.1193 | 0.1193 |
| MAGNESIUM CHLORIDE *6 H2 | 0.1280 | 0.1280 | 0.1280 |
| MAGNESIUM OXIDE | 0.0160 | 0.0160 | 0.0160 |
| L-CARNITINE | 0.0120 | 0.0120 | 0.0120 |
| CHOLINE CHLORIDE | 0.0660 | 0.0660 | 0.0660 |
| MINERAL PREMIX | 0.0430 | 0.0430 | 0.0430 |
| BETA CAROTENE 1% | 0.0130 | 0.0130 | 0.0130 |
| VITAMIN PREMIX | 0.1347 | 0.1347 | 0.1347 |
| STANDARDIZATION WATER | 44.9796 | 44.9896 | 44.9496 |
|  | 100.0000 | 100.0000 |  |

Results
Effect of Starch and Gum Combinations on Serum Separation and Sediment

The control samples containing Melojel starch and guar gum had serum in the top layer as occurs in some such commercial batches. The formulas containing Eurylon 7 starch and guar gum had the least or no serum development compared to those containing Melojel starch. The amount of separation was similar in the samples containing guar or xanthan gum in combination with the Melojel starch.

However, in the sample containing the blend of guar and xanthan gums with Melojel starch the serum separation occurred at a slower rate. The degree of separation was still greater than in the variables containing guar gum and Eurylon 7 starch. Addition of carrageenan to the Melojel starch/guar gum combination significantly reduced the serum separation. Formulas containing either Melojel starch or Eurylon starch without any gum had no serum separation, however salt sediment and slight serum separation was at the bottom of the can and a significant cream separation was evident.

The Eurylon 7 starch and guar gum formulas, which were stable, had similar viscosity to their respective Melojel starch formulas which had separation. Therefore, it appears was still visible and significantly more than samples containing the Melojel starch and guar gum.

TABLE 2

Serum and Viscosity after 3 months storage at 72° F.

| Code | Starch | Use Level | Gum | Use Level | Serum (mls/340 mls) | Viscosity Cp* |
|---|---|---|---|---|---|---|
| 1363-79A | Melojel | 1.6% | Guar | 0.117 | 150 | 47 |
| 1363-80C | Eurylon 7 | 1.1% | Guar | 0.117 | 5 | 44 |
| 1363-109B | Hylon VII | 1.1% | Guar | 0.117 | 5 | 43 |
| 1363-79C | Melojel | 1.6% | Xanthan | 0.117 | 165 | 55 |
| 1363-87C | Eurylon 7 | 1.1% | Xanthan | 0.117 | 5 | 55 |
| 1363-71B | Melojel | 1.6% | Guar/ Xanthan | 0.0525/ 0.0525 | 70 | 55 |
| 1363-71C | Eurylon 7 | 1.1% | Guar/ Xanthan | 0.0525/ 0.0525 | 0 | 72 |
| 1363-79B | Melojel | 1.6% | None | 0 | 20 | 17 |
| 1363-80A | Eurylon 7 | 1.1% | None | 0 | 5 | 12 |
| 1363-72C | Melojel | 1.6% | Guar + Carrageenan | 0.117 | 0 | 52 |

TABLE 2-continued

Serum and Viscosity after 3 months storage at 72° F.

| Code | Starch | Use Level | Gum | Use Level | Serum (mls/340 mls) | Viscosity Cp* |
|---|---|---|---|---|---|---|
| 1363-87B | Melojel | 1.6% | Carrageenan only | 0 | 20 | 19 |

*Viscosity measured using Brookfield LV-DV-1 Viscometer with spindle #1 at 60 rpm; Product temperature @ 70° F.

Figure 2:
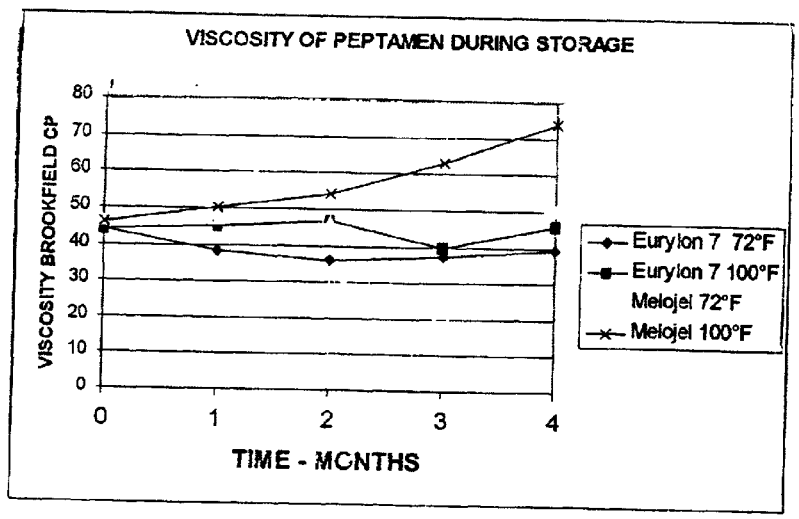
FIG. 2 illustrates graphically viscosity of products during storage pursuant to Example No. 1.

Storage at different temperatures, i.e., 40° F. and 100° F., indicates that Eurylon 7 starch is more stable and does not develop serum at all the tested storage conditions as does Melojel starch. The Melojel starch/guar gum/carrageenan variable which is stable at ambient temperature for 3 months had some serum separation at 40° F., however it is significantly less than without the added carrageenan (50 mls vs 150 mls). The viscosity of the Eurylon 7 does not change significantly during storage at both 72° F. and 100° F. conditions (See FIG. 2). The Eurylon 7 variables also exhibited less viscosity change at 100° F. than the Melojel Starch.

Conclusions

The stability studies after 3 months indicate that in Peptamen®, high amylose starch such as Eurylon 7 and Hylon 7 (National Starch Co.) are more compatible with guar and xanthan gums than is Melojel starch. Adding carrageenan (iota/kappa blend) to the system containing Melojel starch and guar gum is also effective in reducing serum development.

Removing the guar gum from the formula does result in significantly reduced serum, however resulted in sedimentation of the insoluble salts due the low viscosity of the product.

It should be understood that various changes and modifications to the presently preferred embodiments described herein will be apparent to those skilled in the art. Such changes and modifications can be made without departing from the spirit and scope of the present invention and without diminishing its attended advantages. It is therefore intended that such changes and modifications be covered by the appended claims.

We claim:

1. A nutritional product comprising:
   a protein source;
   a lipid source; and
   a carbohydrate source including high amylose starch and guar gum, wherein high amylose starch and guar gum as a total comprise approximately 2.25% to about 7.50% of a total caloric content, and wherein a weight ratio of high amylose starch to guar gum is approximately 2.5:1 to 16:1.

2. The nutritional product of claim 1 wherein:
   the protein source comprises approximately 10% to about 25% of the total calories.

3. The nutritional product of claim 1 wherein the lipid source comprises approximately 25% to about 50% of the total calories.

4. The nutritional product of claim 1 wherein high amylose starch comprises approximately 2.0% to about 6.5% of the total caloric content.

5. The nutritional product of claim 1 wherein guar gum comprises 0.25% to about 1.0% of the total caloric content.

6. The nutritional product of claim 1 wherein the high amylose starch comprises at least approximately 50% by weight amylose.

7. The nutritional product of claim 1 including carrageenan.

8. The nutritional product of claim 1 wherein the carbohydrate source comprises approximately 40 to about 60% of the caloric content.

9. The nutritional product of claim 1 wherein the product is designed to be an enteral product.

10. The nutritional product of claim 1 including xanthan.

11. A nutritional product comprising:
    a hydrolyzed whey protein source;
    a source of lipids; and
    a sufficient amount of a stabilizer to reduce serum separation, the stabilizer including high amylose starch and guar gum, wherein high amylose starch and guar gum as a total comprise approximately 2.25% to about 7.5% of a total caloric content, and wherein a weight ratio of high amylose starch to guar gum is approximately 2.5:1 to 16:1.

12. The nutritional product of claim 11 wherein:
    the protein source comprises approximately 10% to about 25% of the total calories.

13. The nutritional product of claim 11 wherein the lipid source comprises approximately 25% to about 50% of the total calories.

14. The nutritional product of claim 11 wherein high amylose starch comprises approximately 2.0% to about 6.5% of the total caloric content.

15. The nutritional product of claim 11 wherein guar gum comprises 0.25% to about 1.0% of the total caloric content.

16. The nutritional product of claim 11 includes at 1500 Kcals at least 100% of the U.S. RDA of vitamins and minerals.

17. The nutritional product of claim 11 wherein the product includes carrageenan.

18. The nutritional product of claim 11 wherein the carbohydrate source comprises approximately 40 to about 60% of the caloric content.

19. The nutritional product of claim 11 wherein the high amylose starch comprising at least approximately 50% amylose.

20. The nutritional product of claim 11 wherein the product is designed to be an enteral product.

21. The nutritional product of claim 11 including xanthan.

22. A method of stabilizing an enteral solution comprising the steps of adding to an enteral solution a stabilizing amount of high amylose starch and guar gum, wherein high amylose starch and guar gum as a total comprise approximately 2.25% to about 7.50% of the total caloric content.

23. The method of claim 22 wherein high amylose starch comprises approximately 2.0% to about 6.5% of the total caloric content.

24. The method of claim 22 wherein guar gum comprises 0.25% to about 1.0% of the total caloric content.

25. The method of claim 22 wherein the high amylose starch comprises at least approximately 50% by weight amylose.

26. A nutritional product comprising:
    a hydrolyzed whey protein source;
    a source of lipid; and
    a sufficient amount of stabilizer to reduce serum separation, the stabilizer comprising carrageenan, starch and guar gum.

* * * * *